United States Patent [19]
Adel et al.

[11] Patent Number: 5,396,260
[45] Date of Patent: Mar. 7, 1995

[54] VIDEO INSTRUMENTATION FOR THE ANALYSIS OF MINERAL CONTENT IN ORES AND COAL

[75] Inventors: Gregory T. Adel; Roe-Hoan Yoon; Gerald H. Luttrell, all of Blacksburg, Va.

[73] Assignees: The Center for Innovative Technology, Herndon; Virginia Polytechnic Institute & State University; Virginia Tech Intellectual Properties, Inc., both of Blacksburg, all of Va.

[21] Appl. No.: 995,616

[22] Filed: Dec. 22, 1992

[51] Int. Cl.⁶ .......................................... H04N 7/18
[52] U.S. Cl. ........................................... 345/91
[58] Field of Search .............. 358/107; H04N 7/18; 348/86, 91, 128, 135; 73/863.11; 356/36, 243; 250/252.1 A; 406/46

[56] References Cited

U.S. PATENT DOCUMENTS

| | | | |
|---|---|---|---|
| 3,993,899 | 11/1976 | Chapman | 250/227 |
| 4,367,487 | 1/1983 | Klein et al. | 358/107 |
| 4,446,366 | 5/1984 | Brogardh et al. | 250/227 |
| 4,498,778 | 2/1985 | White | 358/107 |
| 4,547,897 | 10/1985 | Peterson | 382/8 |
| 4,617,682 | 10/1986 | Mori et al. | 358/107 |
| 4,672,218 | 6/1987 | Chrisman et al. | 250/574 |
| 4,724,481 | 2/1988 | Nishioka | 358/107 |
| 4,754,329 | 6/1988 | Lindsay et al. | 358/107 |
| 4,776,466 | 10/1988 | Yoshida | 209/565 |
| 4,797,550 | 1/1989 | Nelson et al. | 250/227 |
| 4,797,559 | 1/1989 | Oblad et al. | 250/227 |
| 4,833,322 | 5/1989 | Forster et al. | 356/36 |
| 4,841,140 | 6/1989 | Sullivan et al. | 250/226 |
| 4,951,825 | 8/1990 | Hawkins et al. | 209/558 |
| 5,080,534 | 1/1992 | Goodson et al. | 406/46 |
| 5,091,963 | 2/1992 | Litt et al. | 358/107 |
| 5,161,202 | 11/1992 | Kitakado et al. | 358/107 |
| 5,257,532 | 11/1993 | Hayakawa et al. | 73/863.11 |

Primary Examiner—Howard W. Britton
Assistant Examiner—Richard Lee
Attorney, Agent, or Firm—Whitham, Curtis, Whitham & McGinn

[57] ABSTRACT

Mineral content in processed ore and coal content in coal slurries are determined using a video system. A video image is taken of a sample, the video image is digitized, and gray levels are assigned to points or areas on the video image. The distribution of the gray levels for the image provides an indication of the purity of the minerals in the ore sample. The mean gray level for the image provides an indication of the mineral content of interest in the sample. The video system should be calibrated using ores that normally occur in the process environment and using samples of controlled moisture content. The video system has particular utility in determining phosphate content and calcium ratio in phosphate ores.

24 Claims, 6 Drawing Sheets

FIG.3A  Amine Tailing

FIG.3B  Flotation Feed

FIG.3C  Fatty Acid Concentrate

FIG.3D  Amine Concentrate

VIDEO INSTRUMENTATION FOR THE ANALYSIS OF MINERAL CONTENT IN ORES AND COAL

BACKGROUND OF THE INVENTION

1. Field of the Invention

This invention is generally related to instrumentation for quantitatively determining the mineral content in ore and coal slurries, and has particular application in determining the $P_2P_5$ content and $CaO/P_2O_5$ ratio in phosphate ores.

2. Description of the Prior Art

One third of the world's phosphate production originates from the states of North Carolina and Florida in the United States. Phosphate reserves in North Carolina are concentrated primarily along the Atlantic Coastal Plain. They differ from Florida reserves in that they are generally deeper; however, the uniformity of the deposit tends to make extraction more efficient. Furthermore, the reagent dosages required to upgrade these reserves by froth flotation are usually less than required for Florida phosphate, while the phosphate lost during fine clay removal is about one-tenth of that associated with the Florida ores. However, North Carolina phosphate concentrates generally contain 30-31% $P_2O_5$ as compared to the average Florida grade of around 33%. North Carolina concentrates also have a slightly higher $CaO/P_2O_5$ ratio (calcium ratio) and, therefore, require additional sulfuric acid in the phosphoric acid production step.

A need exists for a suitable means of providing rapid analysis of phosphate grade and calcium ratio in process streams around the flotation circuit. Currently, phosphate grades are either determined in a qualitative manner by inspection (i.e., through the difference in color between the dark phosphate minerals and the light gangue minerals observed by an inspector watching the ore), or in a quantitative manner by wet chemical analysis. In the former case, the determination made is only as accurate as the personal judgement of inspector and this judgement can be affected by the lighting conditions in the plant. Furthermore, slight percentage differences in $P_2O_5$ content are unlikely to be discernible. In the latter case, up to four hours of digestion and analysis may be required to generate an assay. Some common on-line analysis techniques such as X-ray fluorescence and neutron activation have been tested on phosphate ores, but they are generally inaccurate on materials of such low atomic number as calcium and phosphate. On-line nuclear magnetic resonance (NMR) has been used to determine $P_2O_5$ content in slurries; however, this technique has not been successful in providing information on the calcium ratio ($Cao/P_2O_5$).

O'Kane et al., "Preliminary Evaluation of a Computer Vision Sensor for Analysis of Phosphate Tailings", *Control '90—Mineral and Metallurgical Processing*, R. K. Rajamani and J. A. Herbst, eds. SME-AIME, pp. 143-149 (1990), discloses a small image analysis system which can identify different minerals in a sample of phosphate ore. The system requires the ore sample to be carefully spread out in front of a television camera whereby individual grains may be discerned. The minerals are then identified on the basis of the relative color intensities or reflectance from the individual mineral grains, and the quantities present are determined on the basis of the amount of area occupied by each grain in the complete image. Because this technique requires individual grains to be viewed, the quantity of sample which can be analyzed at any given time is small, and using small sample sizes may result in analysis errors because they may not be representative of the bulk stream. Furthermore, the technique is not suitable for on-line use.

On-line instrumentation would also be useful in monitoring coal slurries and other ores.

U.S. Pat. No. 4,797,550 to Nelson et al. discloses a fiber optic detector which is submerged in a coal slurry to monitor a coal separation process. In Nelson et al., light transmitted down a fiber bundle towards the slurry, is scattered by the slurry, and a portion of the light is reflected back to a fiber bundle and detected by a photosensor. The light intensity or hue of gray reflected by the slurry and detected by the photosensor is used to provide an indication of the ash content in the slurry. A disadvantage of the Nelson et al. system is that a small sample must be separated from the slurry and analyzed and, as pointed out above, small samples may not be representative of the bulk stream.

SUMMARY OF THE INVENTION

It is an object of this invention to provide a video camera based analysis system which can be used to quantitatively determine the mineral content in an ore processing stream or coal slurry.

It is another object of this invention to provide a system for quantitatively determining phosphate content and calcium ratio in phosphate ore.

It is another object of this invention to provide particular calibration procedures for making accurate mineral content measurements in an ore processing stream or coal slurry.

According to the invention, a video camera is used to image samples from an ore processing stream or coal slurry or to image the ore processing stream or coal slurry in-situ. The image is digitized and gray levels are assigned to each of the points in the image. The mineral content of particular minerals in an ore processing stream or the coal content in a coal slurry are determined from the distribution of gray levels. The invention has particular application in determining phosphate content and calcium ratio in phosphate ore. It has also been determined that the point in a processing line where the sample is taken and the amount of moisture in the sample can impact on the color of the sample with a resultant affect on gray levels in an image of the sample. Therefore, the invention contemplates calibrating the imaging system for particular sampling locations and for particular moisture levels.

BRIEF DESCRIPTION OF THE DRAWINGS

The foregoing and other objects, aspects and advantages will be better understood from the following detailed description of the preferred embodiments of the invention with reference to the drawings, in which.

DETAILED DESCRIPTION OF THE PREFERRED EMBODIMENTS OF THE INVENTION

The invention utilizes a television camera and computer software to quantitatively determine the concentration of a mineral in a stream of ore or coal slurry or a separated sample thereof. For exemplary purposes, experimental results are presented for a video sensor system which can be used to accurately detect the percent of phosphate and calcium ratio for phosphate ore.

Figure 1:
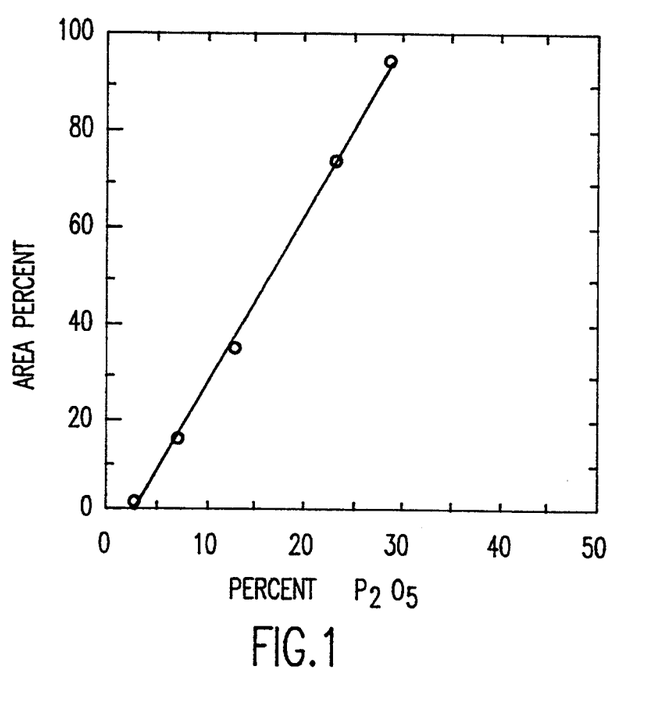
FIG. 1 is a graph showing the relationship between area percent of dark phase and $P_2O_5$ content for dry mixtures of phosphate flotation feed, concentrate, and tailing.

FIG. 1 shows the results of a preliminary experiment where samples of phosphate ore flotation concentrate, feed and tailing were mixed together in various quantities to provide a range of $P_2O_5$ grades for analysis. The mixtures were spread out on a white piece of paper and placed in front of a black and white television camera. Unlike the O'Kane et al. system, no attempt was made to separate individual mineral grains. Different minerals in the sample are detected by their relative darkness or lightness in the image taken by the camera. For example, phosphate minerals are relatively dark and gangue minerals are relatively light. The various shades of gray that comprise the image are given values from 0 to 255 where 0 indicates black and 255 indicates white. These gray shades are known as gray levels, and this invention contemplates using the gray levels to discern information such as phosphate concentration and calcium ratio. The image for each mixture was digitized and stored in a computer with information corresponding to the gray levels for the components of the image. A threshold gray level was chosen to separate the dark phosphate minerals from the light gangue minerals and the image was segmented at this gray level. From this segmented image, the area percent of the dark phase contained in the overall image was determined and plotted versus the actual $P_2O_5$ content of the sample as determined by wet chemical techniques. FIG. 1 shows an excellent correlation was obtained between the area percent of the dark phase (percent having gray level above threshold) and the $P_2O_5$ content of the mixtures.

Figure 2A:
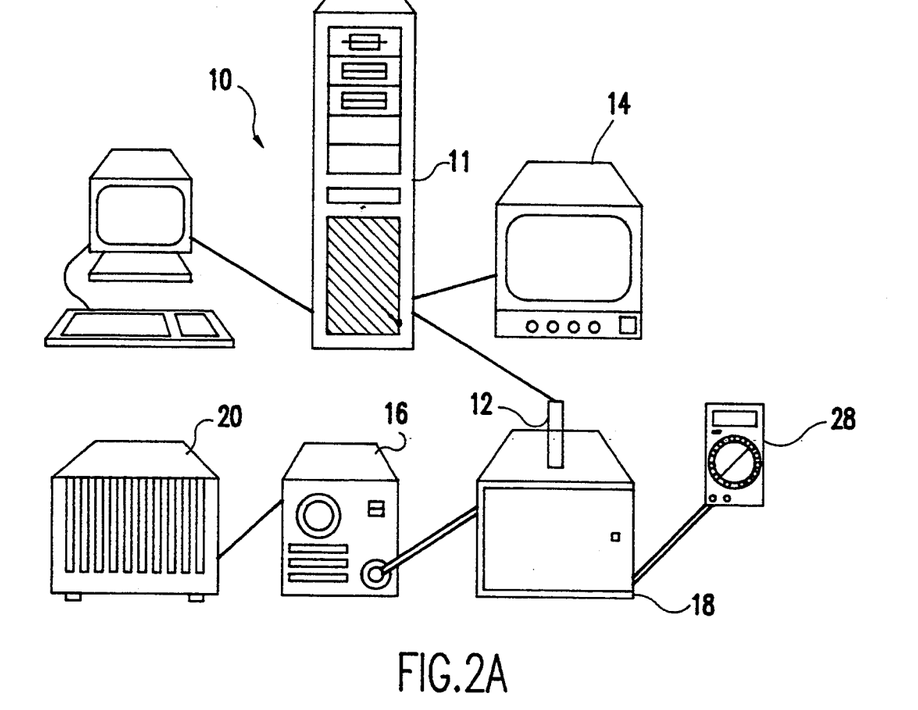
FIGS. 2a and 2b are schematic drawings of a bench top system for analyzing the mineral content in an ore sample and a sample chamber for the bench top system, respectively.

FIG. 2a shows the basic components of a video analysis system according to this invention. The system comprises a computer 10 equipped with frame grabber software and hardware 11, a black-and-white charge coupled display (CCD) television camera 12, a video monitor 14, a fiber optic illuminator 16, and a sample box 18. The camera 12 is connected to the video input port of the frame grabber 11 in the computer 10 while the video monitor 14 is connected to the video output port. The sample inside the sample box 18 is illuminated by the fiber optic illuminator 16 which is powered through a signal conditioner 20. The signal conditioner 20 ensures that line voltage fluctuations do not cause fluctuations in the illumination of the sample.

Figure 2B:
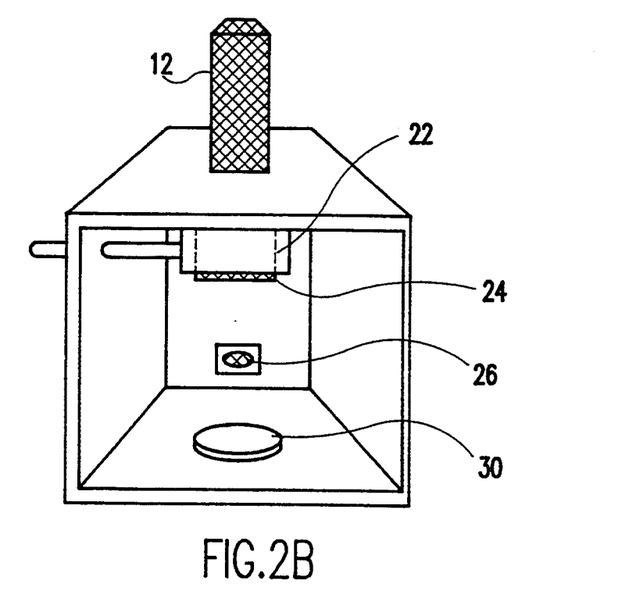
Figure 3A:
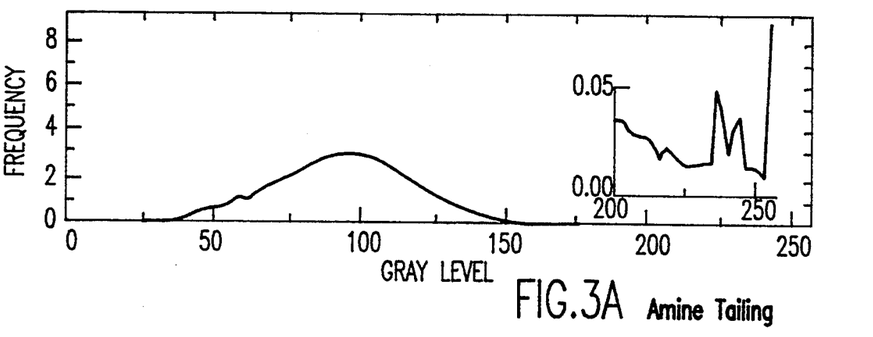
FIGS. 3a–3d are graphs showing the gray level distributions of various phosphate samples.
Figure 3B:
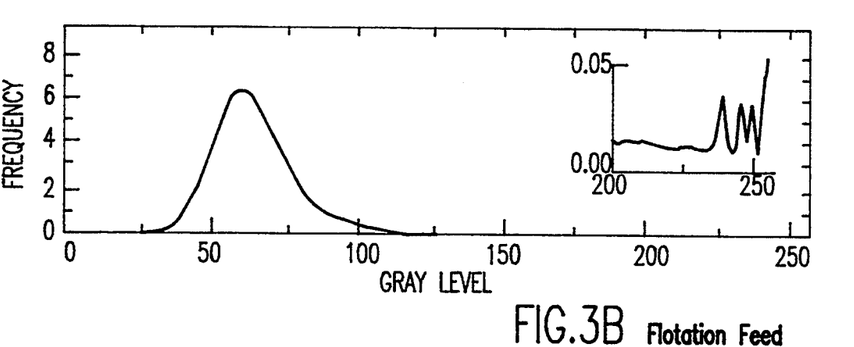
Figure 3C:
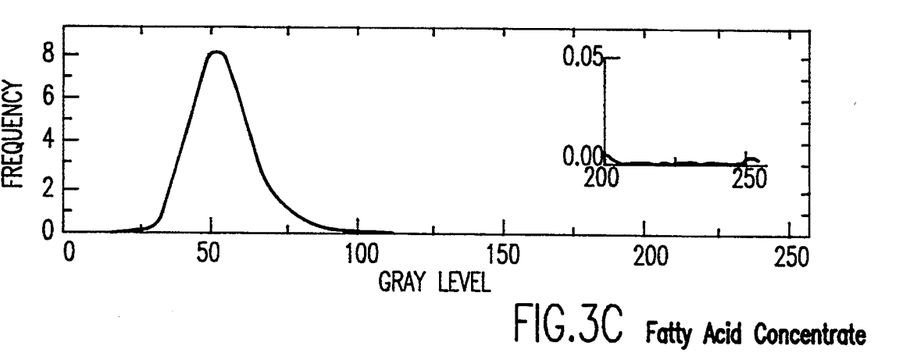
Figure 3D:
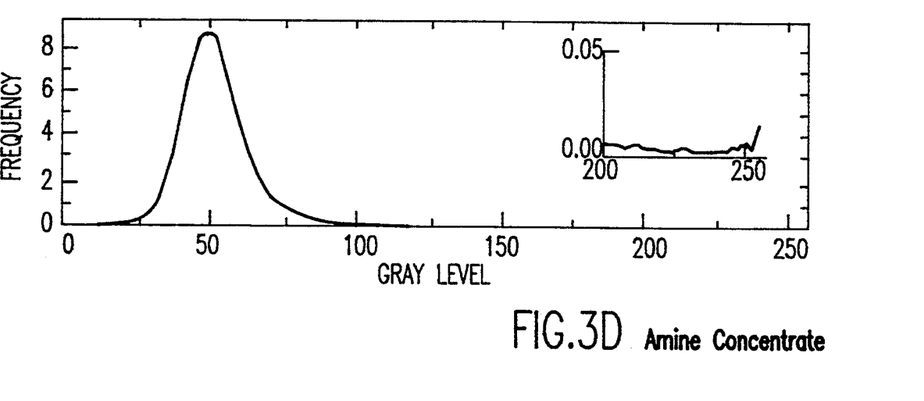

FIG. 2b shows that uniform sample illumination is provided by the fiber optic illuminator 16 via a ring light 22 mounted around the lens 24 of the camera 12. The intensity of incident light is monitored by a photocell 26 mounted in the back wall of the sample box 18. With reference to both FIGS. 2a and 2b, the photocell 26 is connected to a digital multimeter 28. The digital multimeter 28 is used when adjusting the setting on the fiber optic illuminator 16 to prescribed light intensity (e.g., the multimeter provides detected intensity information and the fiber optic illuminator is adjusted in accordance with this intensity information). Adjustments are made to the light intensity as needed to maintain constant illumination of the sample.

Measurements are made with the bench top analyzer of FIG. 2a and 2b by placing a dry sample in container 30 and positioning the container 30 underneath camera 12. The sample is taken from the process stream for the ore or coal slurry. In the case of FIG. 1, flotation concentrate, feed and tailing for phosphate ore were the sample. The sample box 18 door is closed to provide an environment that is free of ambient light. The ring light 22 illuminates the sample and the light setting is adjusted as needed. The camera 12 is used to image the sample, and the image is digitized with the resulting gray level information being processed by the computer 10. Processing of the images collected can be achieved using commercially available software for gray level processing (e.g., OPTIMAS software from Bioscan, Inc., etc.). Image analysis can be carried out interactively using built-in functions of the software or batch applications can be written using a number of different computer languages. Preferably, the computer 10 will selectively display the mineral content information for a single sample as well as an averaged value for several samples. The video monitor 14 provides the operator with a display of the imaged sample. As will be explained below, phosphate content and calcium ratio have been determined with accuracy for several phosphate ore samples and these values are provided on the display screen for the computer 10.

FIGS. 3a-d show gray level distributions obtained from phosphate ore samples taken at different points in a phosphate ore processing circuit. In phosphate ore processing, the ore is subjected to a number of separation and concentration procedures to obtain a more concentrated product of increased purity. FIGS. 3a-d show samples of amine tailing, flotation feed, fatty acid concentrate, and amine concentrate, respectively, and this corresponds to samples with increasing concentration and purity of phosphate. Flotation feed is taken from the processing point where clay is separated from the ore. Fatty acid concentrate is taken from a fatty acid flotation circuit that accomplishes anionic separation and concentration. Amine concentrate and amine tailing are taken from an amine flotation circuit where cationic separation and concentration occurs. FIGS. 3a-d show that the gray level distributions become narrower and shift to lower levels as the $P_2O_5$ content increases. This is due to the increasing amount of dark phosphate mineral present in the samples and the reduction of light-colored calcite and quartz.

If a coal slurry was being examined using the video system of the present invention, one would expect to find narrower distributions and lower gray levels when the coal content increases and impurities such as ash are removed. This is explained by the fact that coal is dark and ash is light in color.

The inset graph in FIGS. 3a-d show the upper end of the gray level spectrum (e.g. 200-255). Low level peaks can be seen near the 250 gray level, and these peaks are the result of nearly white calcite (CaO) particles in the samples. The peaks are highest for the amine tailing and flotation feed where the phosphate is the least pure. The calcite peak increases slightly for the amine concentrate relative to the fatty acid concentrate sample because quartz is rejected at this part of the processing circuit, thereby causing the calcite content to increase in the sample.

Figure 4:
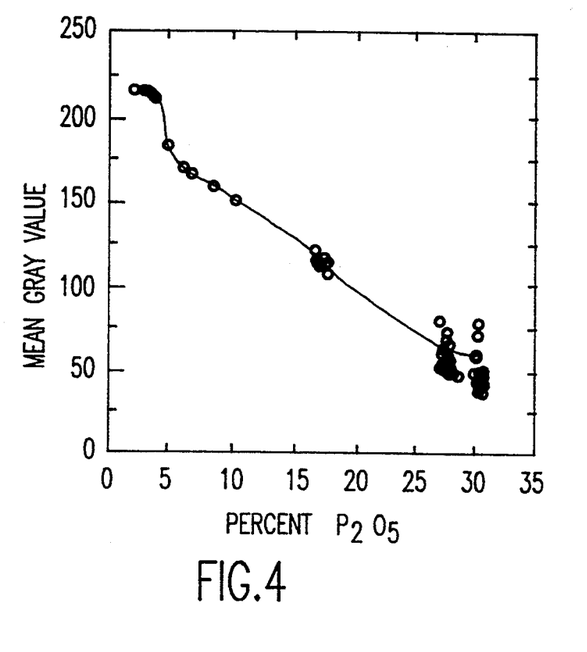
FIG. 4 is a graph showing the relationship between the mean gray level and the phosphate content for a number of phosphate samples.

FIG. 4 shows the correlation between the $P_2O_5$ content and mean gray level for several samples of phosphate ore taken at different processing points in a phosphate ore flotation circuit. The percent $P_2O_5$ was determined using conventional wet chemical analysis procedures and the mean gray level is the average gray level present in the digitized image of the sample. FIG. 4 clearly shows that as the percentage of $P_2O_5$ in a processing stream increases, the mean gray value decreases, and that when the percentage of $P_2O_5$ in a sample is low, the mean gray value is high. Hence, by imaging the sample of phosphate ore and determining the mean gray value for that image, the percentage of $P_2O_5$ for the sample can be determined.

The relationship shown in FIG. 4 is not completely linear. The scattering and deviation from linearity in the correlation between mean gray value and percent $P_2O_5$ is related to natural variations in the ore body as phosphate is mined. Specifically, as the ore is mined, the relationship between color of the phosphate and percent $P_2O_5$ may change slightly. The amount of stained quartz present in the ore may also change. These changes cause the data points in the calibration curves to scatter. If the changes in the ore body are great, new calibration curves should be generated. Preparing calibration curves periodically, e.g., monthly, may be a suitable processing plant procedure. Another factor to be considered is the need to calibrate the video instrumentation for individual streams generated in the plant. Each step of the phosphate separation process separates a different component of the ore. For example, the fatty acid flotation is used to separate phosphate mineral and some quartz away from calcite. This is followed by amine flotation where the quartz is floated away from the phosphate mineral. Because these separation steps are directed at different components of the ore, they can be affected differently as the composition of the ore varies. Hence, it is most advantageous to calibrate the video instrumentation for a given stream than to have one overall calibration for an entire plant.

For example, since the fatty acid and amine concentrates are of primary interest in phosphate ore processing, separate calibration curves should be developed for each stream. This is accomplished by taking two or more samples of fatty acid concentrate from the fatty acid flotation circuit and two or more samples of amine concentrate from the amine flotation circuit, determining $P_2O_5$ content for the samples by wet chemical or other laboratory techniques, imaging the samples with the video camera, determining mean gray levels for the images, and correlating the mean gray levels with the known $P_2O_5$ content. A calibration curve is developed from the mean gray levels for samples having known $P_2O_5$ content. Subsequent samples from the fatty acid flotation circuit and the amine flotation circuit of unknown $P_2O_5$ content can then be imaged, and the mean gray level for those samples is compared with the calibration curve for that feed material.

For phosphate ores, experimentation has shown that for $CaO/P_2O_5$ calibration (as opposed to $P_2O_5$ calibration), a single calibration curve can be used for both fatty acid and amine concentrates. This is based on a linear trend when results for the two types of samples were combined. With reference back to the inset graphs in FIGS. 3a–d, the area under the calcite peak, which is the percent of the image with a gray level greater than 210, was used to determine calcite content in the samples. A calibration curve is prepared by imaging ore samples of known calcite content and relating the area under the calcite peak to the known calcite content. The calcite peak found in later samples is then compared to this calibration curve. Calcium ratio is simply computed as weight percent $CaO$/weight percent $P_2O_5$.

All calibration curves required for mineral analysis for the ore stream or coal slurry are preferably entered into the computer controller for the video imaging system. Calibration curves can be determined periodically on a daily or hourly basis to enhance the accuracy of the imaging system. In the analysis of phosphate ores, it has been found to be advantageous to enter the calibration curves using a cubic spline algorithm. Although linear relationships can be used for all calibrations, the cubic spline algorithm provides additional flexibility if a nonlinear relationship is ever required. Table 1 shows that the video imaging system of this invention has produced highly accurate results for determining phosphate content and calcium ratio in fatty acid concentrate and amine concentrate produced when processing phosphate ore.

TABLE 1

| Stream | Assay |
| --- | --- |
| Fatty Acid Concentrate ($P_2O_5$) | 27.6 ± 0.14% |
| Amine Concentrate ($P_2O_5$) | 30.3 ± 0.05% |
| Amine or Fatty Acid Conc. (Ca ratio) | 1.62 ± 0.003 |

The results in Table 1 are based on 90% confidence interval.

The results in Table 1 were obtained with dry samples of phosphate ore. Dry samples are prepared by collecting approximately 450 g (1 lb). of wet concentrate, drying the sample in a microwave oven, and then distributing the sample on four to six laboratory watch glasses for video imaging. The process takes 8–10 minutes. In contrast, wet samples have been prepared by vacuum drying of the sample to create a filter cake for imaging. Unfortunately, it was initially observed that the accuracy of the video imaging system for determining phosphate content and calcium ratio in wet phosphate ore samples from the filter cake was suspect. Similar to the discussion above in conjunction with FIG. 4 where the point of sampling in the process stream was found to be important in making an accurate calibration curve, it has been found that the moisture content of the sample has an effect on the color of the sample. Therefore, the inaccuracies encountered with the video imaging system on wet samples of phosphate ore can be explained as being the result of variable moisture content in different samples resulting from the vacuum drying procedure. Hence, accurate results can be obtained with wet samples, provided the moisture content of the sample is the same as the moisture content of the samples used to make the calibration curve. Being able to monitor wet samples would be advantageous in processing line because there would be less time required for analysis. Furthermore, if the video imaging system is to be implemented on-line, the processed ore stream will generally be wet in-situ. In an on-line implementation of the video imaging system of this invention, the moisture content of the stream at the site of the video imaging system would be determined and the standard samples used for calibration would be adjusted to that moisture content.

Figure 5:
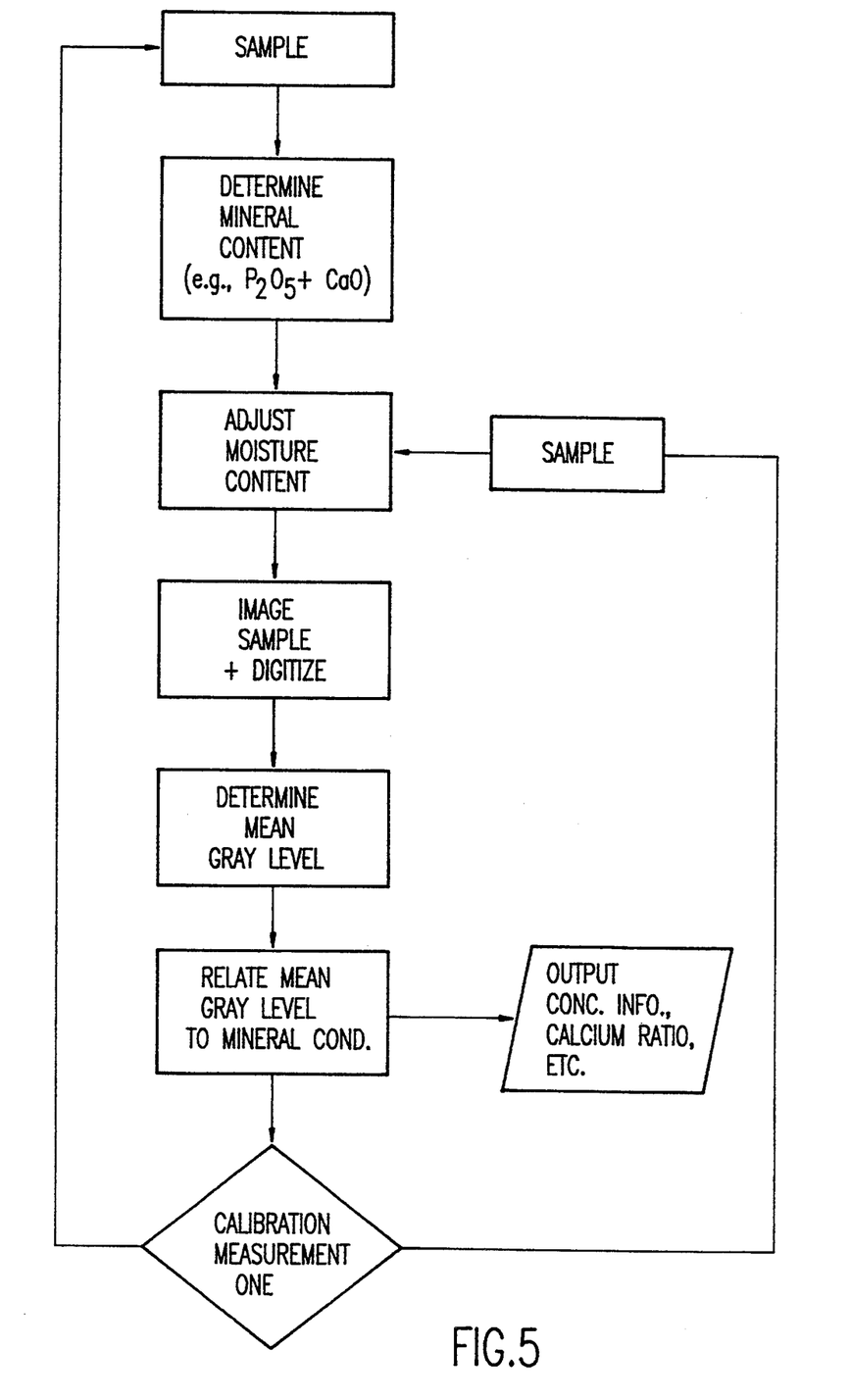
FIG. 5 is a flow chart showing process steps for using the video system of the present invention.

FIG. 5 shows a process scheme for the video imaging system of the present invention which can be used to identify mineral ore content in an ore processing system (e.g., $P_2O_5$ concentration and calcium ratio in phosphate ores, etc.) or coal content in a coal slurry. A sample from the processing stream is taken and its mineral content is determined by wet chemistry or other laboratory techniques. As pointed out above in conjunction with FIG. 4, this sample is used for calibration and should be the result of normal processing of the ore or slurry (e.g., the fatty acid concentrate and amine concentrate in a phosphate ore processing circuit). The moisture level of the sample is determined and may be adjusted to a preset value. The sample is then imaged with the video camera, the image is digitized, and the mean gray level for the image is determined. The mean gray level is then correlated with the mineral content determined using the wet chemistry or other laboratory method and output to a display, printer, chart recorder, or the like. The process is continued until a sufficient number of samples are tested, video imaged, and correlated so that a calibration curve for the sample stream can be stored. Thereafter, samples of unknown mineral content are taken from the processing stream at the same site as the calibration samples. These samples are adjusted to the prescribed moisture content, then imaged, digitized, and a mean gray level is determined. The mineral content for the samples is then determined from comparing the measured mean gray level with the calibration curve. Calculations, such as determining the calcium ratio, from the measured mineral content can be performed by the computer process controller and output to the display.

Figure 6:
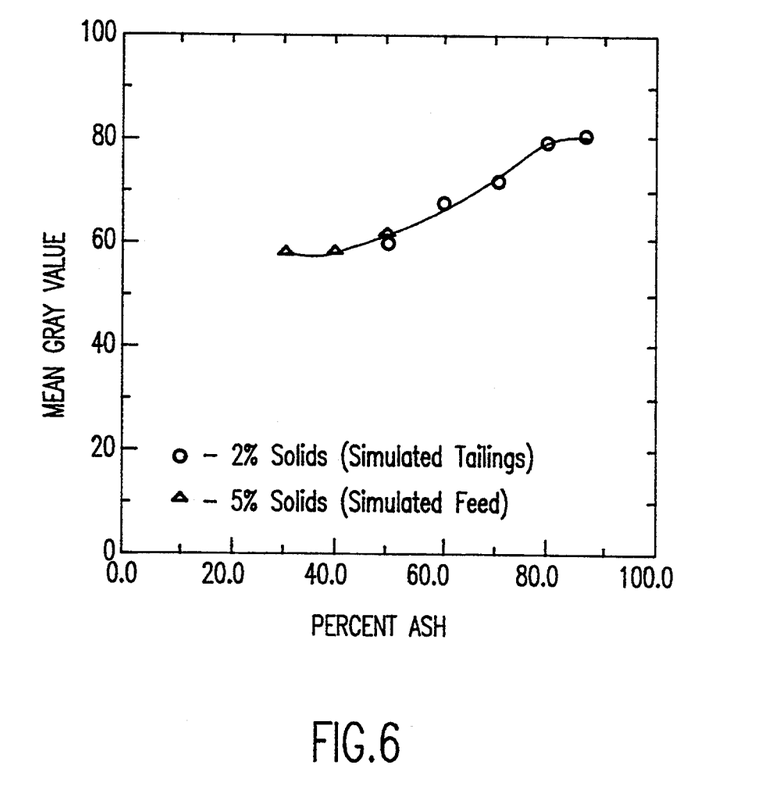
FIG. 6 is a graph showing the correlation between the mean gray value and ash content in simulated fine coal tailings and feed slurries.

FIG. 6 presents test results that demonstrate the video instrumentation described above can be used for on-line analysis of the ash content in fine coal slurries. In this work, beakers of coal slurry containing various levels of ash were placed on a magnetic stirrer plate and presented to the video sensor. Those samples containing 50–80% ash were slurried at 2% solids to simulate a typical flotation tailings stream, while those samples containing 30–50% ash were slurried at 5% solids to simulate a flotation feed. The slurries were created from -325 mesh samples of flotation tailing and concentrate generated from column flotation work. The results in FIG. 6 indicate an excellent correlation between gray value and ash content. Based on the slope of the curve, it appears that the resolution for the tailings samples is much better than that for the feed samples; however, by adjustments to sample presentation and lighting, it should be possible to improve the resolution for both analyses. At present, the data indicate that it may be possible to measure differences in tailings ash as low as 1%. It is also noted that there is very little difference between the two points obtained at 50% ash for different values of percent solids, which indicates that percent solids of the stream will not adversely impact on the mean gray value measurement.

Figure 7:
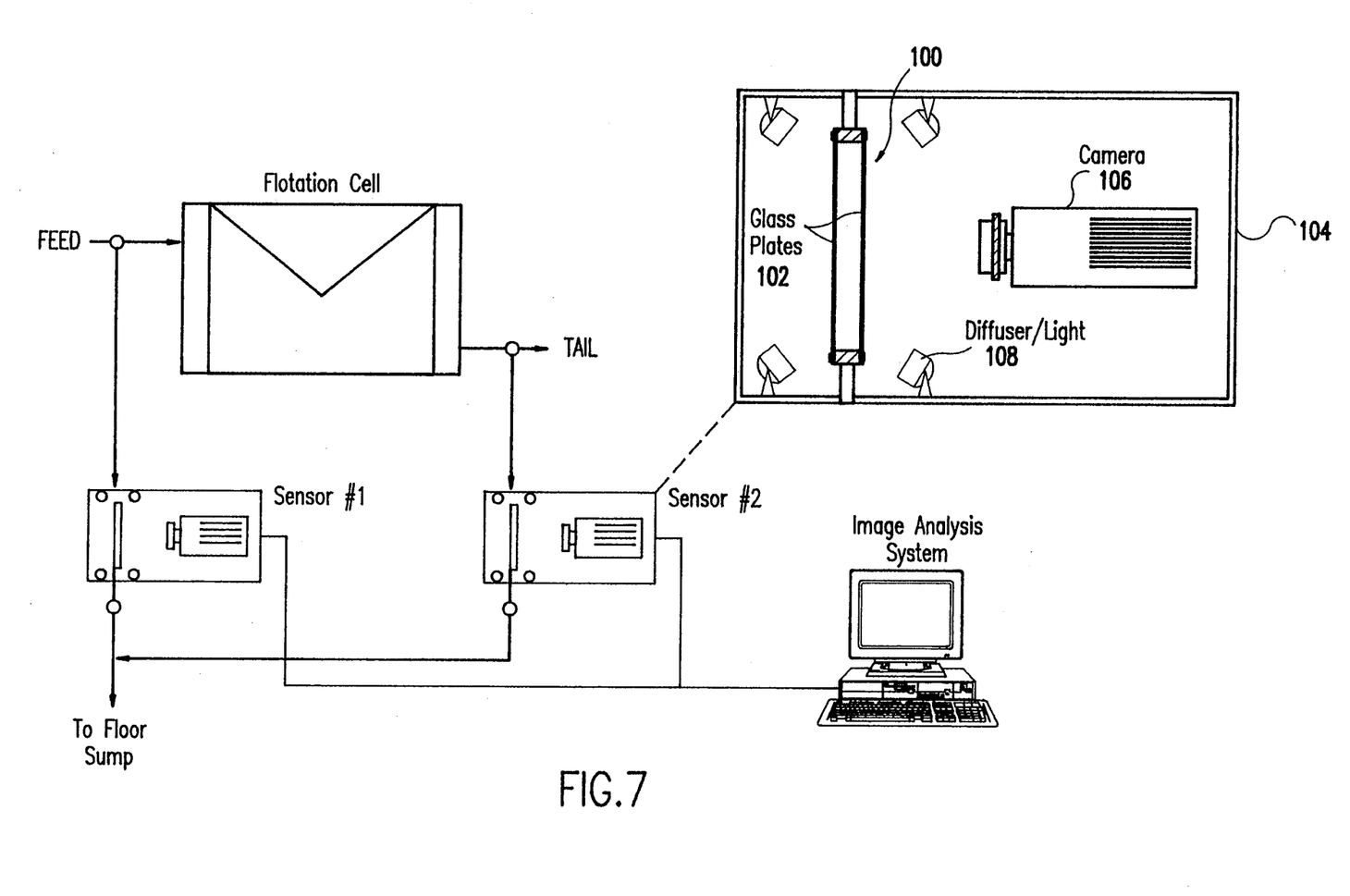
FIG. 7 is a schematic diagram showing a sample presentation system to be used on-line in a processing plant environment.

FIG. 7 shows one exemplary arrangement by which the video instrumentation system of the present invention implemented for on-line use. In particular, slip streams are extracted from the tailings and feed lines and allowed to pass through a thin sample chamber 100 with flat glass plates 102 on either side. The sample chamber 100 is enclosed in a light-tight box 104 with a video camera 106 and means for illuminating the sample (preferably diffuser lights 108). The lights on the camera side of the sample are illuminated to provide a reflected light image of the sample for ash analysis. These lights are then turned off and the lights behind the sample are illuminated to provide a transmitted light image for determining percent solids, if necessary. It may also be possible to determine percent solids directly from the reflected light image. In addition, two separate cameras may be used for analyzing the feed and tailings streams. Images from separate cameras can be sent to the image analysis hardware through a multiplexer or other hardware.

While the invention has been described in terms of its preferred embodiments, those skilled in the art will recognize that the invention can be practiced with modification within the spirit and scope of the appended claims.

Having thus described our invention, what we claim as new and desire to secure by Letters Patent is as follows:

1. An apparatus for determining mineral content in ore, comprising:
   a camera;
   means for illuminating a sample of said ore which allows said camera to produce an image of said sample;
   means for determining gray levels for points in said image;
   means for determining a mean gray level for said image; and
   means for determining mineral content from said mean gray level.

2. An apparatus as recited in claim 1 wherein said means for illuminating includes a means for maintaining a constant light intensity directed towards said sample.

3. An apparatus as recited in claim 2 wherein said means for maintaining a constant light intensity includes a means for sensing an intensity of light emanating from said means for illuminating.

4. An apparatus as recited in claim 1 wherein said means for illuminating includes a line conditioner which prevents variations in power supplied to said means for illuminating from altering light output from said means for illuminating.

5. An apparatus as recited in claim 1 wherein said means for determining mineral content from said mean gray level includes a means for storing calibration information which relates gray levels to mineral content.

6. An apparatus as recited in claim 1 further comprising a means for adjusting a moisture content of said sample to a preset value.

7. An apparatus as recited in claim 1 wherein said sample is a phosphate ore and said means for determining mineral content provides a phosphate concentration and a calcium ratio for said phosphate ore.

8. A process for determining mineral content in ore, comprising the steps of:
   imaging a sample of said ore with a camera;
   determining gray levels for points in an image produced during said imaging step;
   determining a mean gray level for said image; and
   determining a mineral content from said mean gray level.

9. A process as recited in claim 8 further comprising the step of calibrating gray levels for said sample with said mineral content.

10. A process as recited in claim 9 wherein said step of calibrating includes adjusting a moisture content of said sample to a preset value.

11. A process as recited in claim 9 wherein said step of calibrating includes:
obtaining samples of said ore taken from a particular point in a processing stream where said sample which is imaged during said imaging step is taken;
determining a mineral content for said samples;
imaging said samples;
determining gray levels for points in images of said samples produced during said imaging step;
determining a mean gray level for said images of said samples; and
correlating said mean gray level for said images of said samples with said mineral content of said samples determined during said determining step.

12. A process as recited in claim 11 wherein said sample is phosphate ore and further comprising the step of providing both a phosphate content and a calcium ratio for said sample.

13. An apparatus for determining coal content in coal slurdes, comprising:
a camera;
means for illuminating a sample of a coal slurry which allows said camera to produce an image of said sample;
means for determining gray levels for points in said image;
means for determining a mean gray level for said image; and
means for determining coal content from said mean gray level.

14. An apparatus as recited in claim 13 wherein said means for illuminating includes a means for maintaining a constant light intensity directed towards said sample.

15. An apparatus as recited in claim 14 wherein said means for maintaining a constant light intensity includes a means for sensing an intensity of light emanating from said means for illuminating.

16. An apparatus as recited in claim 13 wherein said means for illuminating includes a line conditioner which prevents variations in power supplied to said means for illuminating from altering light output from said means for illuminating.

17. An apparatus as recited in claim 13 wherein said means for determining coal content from said mean gray level includes a means for storing calibration information which relates gray levels to said coal content.

18. An apparatus as recited in claim 13 further comprising a means for adjusting a moisture content of said sample to a preset value.

19. An apparatus as recited in claim 13 wherein said sample is a phosphate ore and said means for determining coal content provides a phosphate concentration and a calcium ratio for said phosphate ore.

20. A process for determining coal content in coal slurdes, comprising the steps of:
imaging a sample of a coal slurry with a camera;
determining gray levels for points in an image produced during said imaging step;
determining a mean gray level for said image; and
determining a coal content from said mean gray level.

21. A process as recited in claim 20 further comprising the step of calibrating gray levels for said sample with said coal content.

22. A process as recited in claim 21 wherein said step of calibrating includes adjusting a moisture content of said sample to a preset value.

23. A process as recited in claim 21 wherein said step of calibrating includes:
obtaining samples of said coal slurry taken from a particular point in a processing stream where said sample which is imaged during said imaging step is taken;
determining a coal content for said samples;
imaging said samples;
determining gray levels for points in images of said samples produced during said imaging step;
determining a mean gray level for said images of said samples; and
correlating said mean gray level for said images of said samples with a coal content of said samples determined during said determining step.

24. A process as recited in claim 23 wherein said sample is phosphate ore and further comprising the step of providing both a phosphate content and a calcium ratio for said sample.

* * * * *